(12) United States Patent
Ridha

(10) Patent No.: US 11,395,670 B2
(45) Date of Patent: Jul. 26, 2022

(54) TONSILLECTOMY SUCTION DISSECTOR APPARATUS

(71) Applicant: Hayder Ridha, Dubbo (AU)

(72) Inventor: Hayder Ridha, Dubbo (AU)

( * ) Notice: Subject to any disclaimer, the term of this patent is extended or adjusted under 35 U.S.C. 154(b) by 141 days.

(21) Appl. No.: 16/632,854

(22) PCT Filed: May 22, 2018

(86) PCT No.: PCT/AU2018/050487
§ 371 (c)(1),
(2) Date: Jan. 21, 2020

(87) PCT Pub. No.: WO2019/018877
PCT Pub. Date: Jan. 31, 2019

(65) Prior Publication Data
US 2021/0307770 A1    Oct. 7, 2021

(30) Foreign Application Priority Data

Jul. 22, 2017    (AU) ................................ 2017902866

(51) Int. Cl.
*A61B 17/26*    (2006.01)
*A61B 17/3211*    (2006.01)

(52) U.S. Cl.
CPC ..... *A61B 17/26* (2013.01); *A61B 2017/32113* (2013.01); *A61B 2217/005* (2013.01)

(58) Field of Classification Search
CPC .............. A61B 17/26; A61B 2217/005; A61B 2017/32113
See application file for complete search history.

(56) References Cited

U.S. PATENT DOCUMENTS

| | | | |
|---|---|---|---|
| 4,307,720 A | 12/1981 | Weber | |
| 5,318,565 A * | 6/1994 | Kuriloff | A61B 18/1402 604/119 |
| 6,293,945 B1 * | 9/2001 | Parins | A61B 18/1402 606/49 |
| 9,247,954 B2 | 2/2016 | Nallakrishnan | |
| 10,413,313 B2 * | 9/2019 | Brown et al. | A61B 17/3421 |

(Continued)

OTHER PUBLICATIONS

International Search Report dated Aug. 6, 2018 from corresponding PCT Application No. PCT/AU2018/050487.

(Continued)

*Primary Examiner* — Shaun L David
*Assistant Examiner* — Mitchell Brian Hoag
(74) *Attorney, Agent, or Firm* — Innovation Capital Law Group, LLP; Vic Lin

(57) ABSTRACT

A tonsillectomy suction dissector apparatus (100) having a proximal handle (101) and a distal curved tip (102) which has a suction channel (103) within and along the tip connecting at least one suction inlet port (105) to a vacuum port. The apparatus has a flexible cutting blade member (106) slidably retained and orientated widthwise within a corresponding slot (107) and configurable by hand operable locking mechanism (108) between an extended position wherein a distal cutting end (109) of the cutting blade member extends from the end of the tip and a retracted position. The shape and orientation of the blade allows the blade to bend within the slot when being extended for cutting.

19 Claims, 7 Drawing Sheets

(56) References Cited

U.S. PATENT DOCUMENTS

| | | | |
|---|---|---|---|
| 2014/0182140 A1* | 7/2014 | Rosenhan | A61B 17/3213 30/162 |
| 2014/0276763 A1* | 9/2014 | Greep | A61C 1/14 606/1 |
| 2015/0335376 A1* | 11/2015 | Hufnagel | A61B 18/1206 606/39 |
| 2016/0081710 A1* | 3/2016 | Barnes | A61B 17/320036 606/170 |
| 2016/0235431 A1* | 8/2016 | Brown | A61B 17/320016 |
| 2018/0177497 A1* | 6/2018 | Swift | A61B 17/02 |
| 2019/0021749 A1* | 1/2019 | Khanicheh | A61B 17/12022 |
| 2019/0099209 A1* | 4/2019 | Witt | A61B 18/082 |

OTHER PUBLICATIONS

Extended European Search Report dated Feb. 2, 2021 from European Application No. 18838057.0.

* cited by examiner

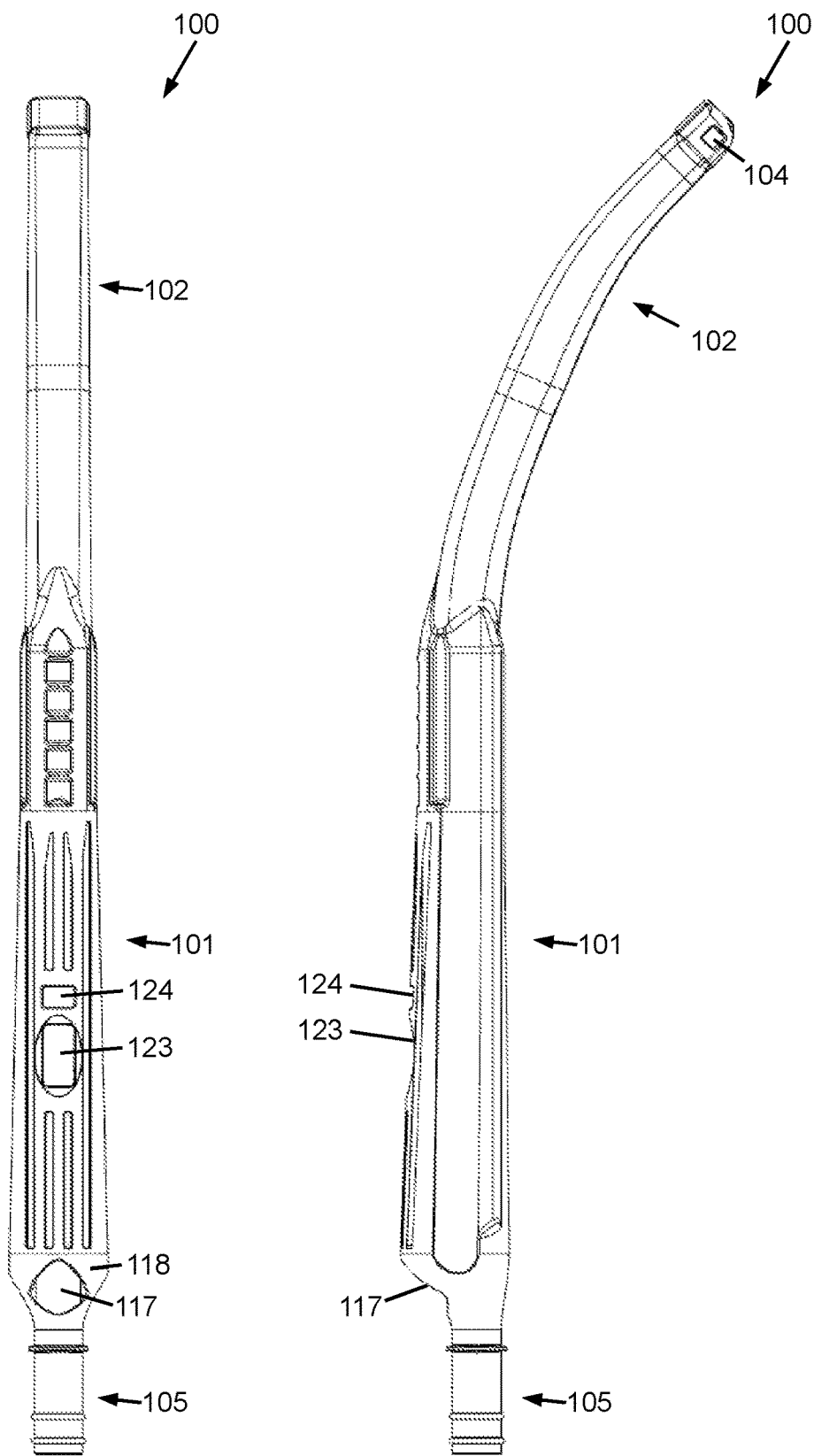
Figure 3                    Figure 4

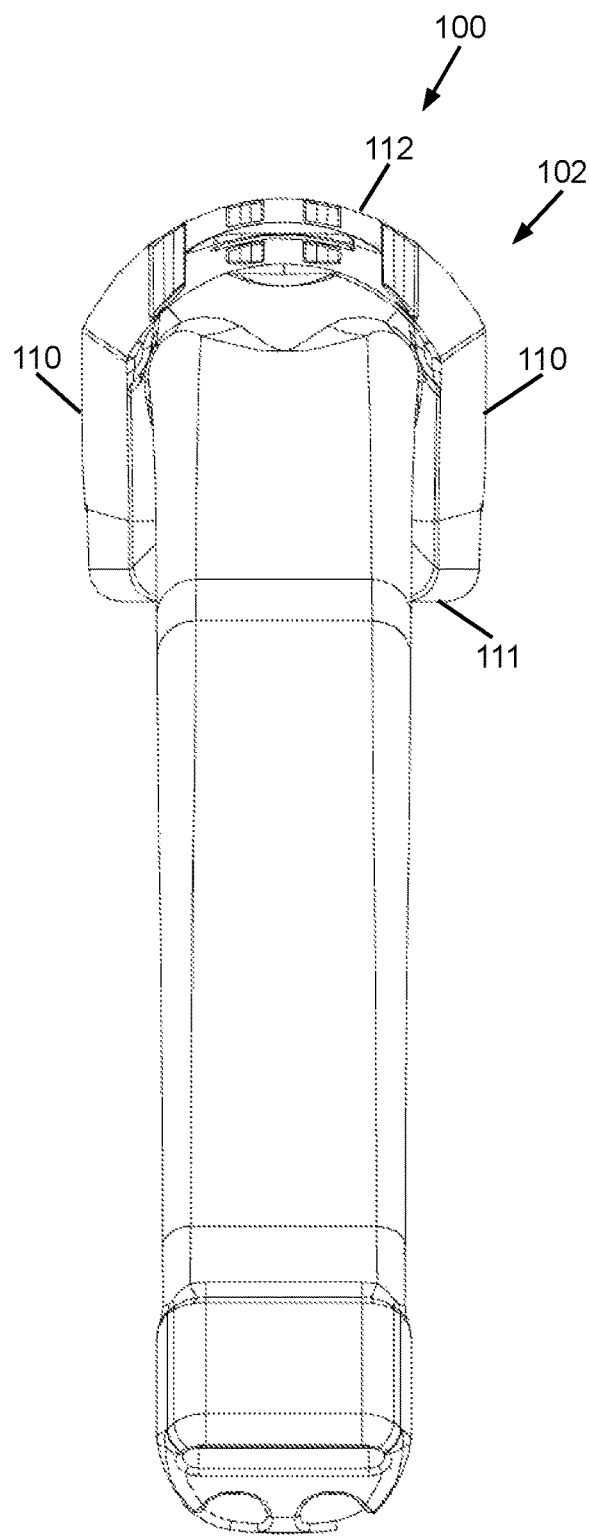
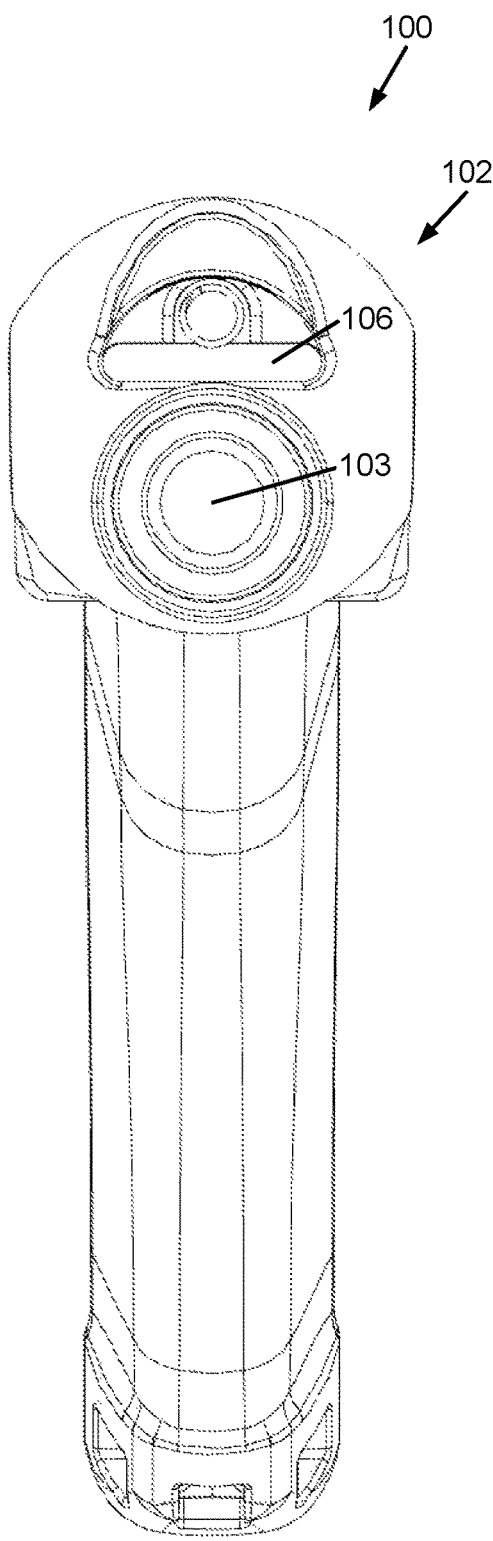
Figure 5
Figure 6

TONSILLECTOMY SUCTION DISSECTOR APPARATUS

FIELD OF THE INVENTION

This invention relates generally to tonsillectomy apparatus. More particularly, this invention relates to tonsillectomy apparatus selectively configurable between dissection and suction and suction only modes of use.

BACKGROUND OF THE INVENTION

Tonsillectomy is a surgical procedure in which both palatine tonsils are removed from a recess in the side of the pharynx called the tonsillar fossa.

One type of tonsillectomy procedure comprises the use of an elongate cutting blade for the dissection of the tonsils, typically held in one hand whilst another hand uses forceps to hold the tonsils.

A vacuum suction tip may be used to remove fluids (blood and saliva) during the procedure. The Yankauer tip (tonsil tip) is one of the most commonly used suction tips.

However, the utilisation of three instruments requires an assistant or alternatively the substitution of instrumentation as required, complicating and prolonging the procedure.

Furthermore, whilst the Yankauer tip allows for aspiration of large volumes of fluid, the Yankauer tip has the disadvantage of easily occluding when the tip is brought into close approximation with tissues or large blood clots. Surgeons often place a gauze sponge over the tip and suctioning fluid through the gauze to prevent occluding clogging.

The present invention seeks to provide a tonsillectomy suction dissector apparatus, which will overcome or substantially ameliorate at least some of the deficiencies of the prior art, or to at least provide an alternative.

It is to be understood that, if any prior art information is referred to herein, such reference does not constitute an admission that the information forms part of the common general knowledge in the art, in Australia or any other country.

SUMMARY OF THE DISCLOSURE

There is provided herein a tonsillectomy suction dissector apparatus comprising a proximal handle and a distal curved tip. The apparatus comprises a suction channel within and along the tip operably connecting at least one suction inlet port located at the end of the tip to a vacuum port of the handle for the suction of fluid in use. The apparatus further comprises a flexible cutting blade member slidably retained and orientated widthwise within a corresponding widthwise and lengthwise slot along the tip and configurable by hand operable locking mechanism between an extended position wherein a distal cutting end of the cutting blade member extends from the end of the tip and a retracted position wherein the distal cutting end of the flexible cutting blade member is retracted within an end of the tip.

This retraction and extension of the blade allows dual functionality as suction tip or suction dissector, thus speeding the operation and reducing blood loss.

As such, the locking mechanism may be used for quickly reconfiguring the apparatus between dissection and suction and suction only modes of operation. Furthermore, the present configuration allows for one-handed dissection and suctioning, freeing the other hand for other tasks, such as manipulating forceps.

Furthermore, the present locking mechanism may allow for the reconfiguration of the apparatus with one hand, such as using the thumb only, freeing the forefingers for gripping the handle.

Specifically, the locking mechanism may comprise the flexible cutting blade member comprising a locking lever which locks within superior apertures of the handle. The cutting blade member extends from a rear aperture of the handle for pushing forwards to the extended position wherein the locking lever locks within the superior apertures. Furthermore, the locking lever is accessible via the superior apertures to disconnect and pull the lever rearwardly to retract the cutting blade member.

The position of the suction holes towards the tonsillar fossa, where the bleeding happens, allowed instant suction of the blood at the exactly bleeding point, thus minimising the chance of blood accumulating in the throat, reducing risk of blood/clot inhalation.

Also, the position of the blade towards the surgeon, allows precise dissection and full visibility of the cutting place at all time, reducing the chance of inadvertently injuring surrounding tissues, and causing further bleeding Furthermore, the configuration of the suction inlet ports may substantially reduce or eliminate occlusion problems as may be experienced by the Yankauer tip. Specifically, the suction inlet ports may be located inferiorly with respect to the distal cutting end and may be arranged on differing faces of the end of the tip so as to prevent occlusion by pressing against one surface thereof. Specifically, in embodiments, the suction inlet ports may comprise a pair of distally located, oppositely laterally located and inferiorly located suction inlet ports.

According to one aspect, there is provided tonsillectomy suction dissector apparatus comprising a proximal handle and a distal curved tip; a suction channel within and along the tip operably connecting at least one suction inlet port located at the end of the tip to a vacuum port at the handle; and a flexible cutting blade member slidably retained within a slot within and along the tip and configurable by a hand operable locking mechanism between an extended position wherein a distal cutting end of the flexible cutting blade member extends from the end of the tip and a retracted position wherein the distal cutting end of the flexible cutting blade member is retracted within the end of the tip, wherein the locking mechanism comprises: the cutting blade member comprising a locking lever able to be depressed via at least one superior aperture within the handle, the locking lever configured such that depressing the lever when the cutting blade member is in the extended position unlocks the cutting blade member to allow the cutting blade member to be retracted; and a proximal end of the cutting blade member extends via a rearward aperture of the handle, the rearward aperture facing rearwards, such that pushing the proximal end forwardly when the cutting blade member is in the retracted position slides the cutting blade member forwardly.

The at least one superior aperture may comprise a rearward superior aperture and a forward superior aperture and wherein the lever may comprise a rearward knob accessible via the rearward superior aperture and an arrowhead boss orientated to catch against a rear edge of the forward superior aperture when the cutting blade member may be in the extended position and to slide under a front edge of the rearward superior aperture when the cutting blade member transitions from the retracted to the extended position.

The rearward superior aperture may be sufficiently elongate such that the rearward knob locates between rearward and forward edges thereof between the retracted and extended positions.

The forward superior aperture may be smaller than the rearward superior aperture.

The rearward knob may comprise a forward edge accessible within the rearward superior aperture against which the cutting blade member can be pulled rearwardly to the retracted position.

The cutting blade member may be pulled entirely from the rearward aperture.

The lever may be pivotally retained by a live hinge.

The lever may comprise a forward buttress which abuts against an opposing wall when the cutting blade member may be at the extended position.

The proximal end may lie flush with the rearward aperture when the cutting blade member may be at the extended position.

The flexible cutting blade member may comprise a flattened portion flexibly orientated widthwise within the slot.

The flexible cutting blade member may comprise plastic.

The flexible cutting blade member may comprise a thickness of approximately 3 mm.

The flexible cutting blade member may comprise a width of approximately 10 mm.

The apparatus may comprise a two-piece construction comprising a first piece comprising the integrally formed handle and tip and a second piece comprising the cutting blade member.

The distal cutting end may narrows towards an orthogonal straight cutting edge.

The cutting edge may comprise a length of approximately 10 mm.

The cutting edge may comprise serrations.

The serrations may be arranged substantially along the width of the cutting edge and transition from top to bottom of the edge.

The at least one suction inlet port may be located inferiorly with respect to the distal cutting end and wherein the at least one suction inlet port may comprise a plurality of suction inlet ports comprising at least one of distally, laterally and inferiorly located suction inlet ports.

A method of performing a tonsillectomy using the present apparatus may comprise, with one hand, pushing the proximal end of the cutting blade member forwardly to perform simultaneous dissection and suction and retracting the cutting blade member by depressing the lever to perform suction only.

Other aspects of the invention are also disclosed.

BRIEF DESCRIPTION OF THE DRAWINGS

Notwithstanding any other forms which may fall within the scope of the present invention, preferred embodiments of the disclosure will now be described, by way of example only, with reference to the accompanying drawings in which:

FIG. 3 illustrates a top plan view of the apparatus;

FIG. 4 illustrates a side elevation view of the apparatus;

FIG. 5 shows a front elevation view of the apparatus;

FIG. 6 shows a rear elevation view of the apparatus;

DESCRIPTION OF EMBODIMENTS

Figure 1:
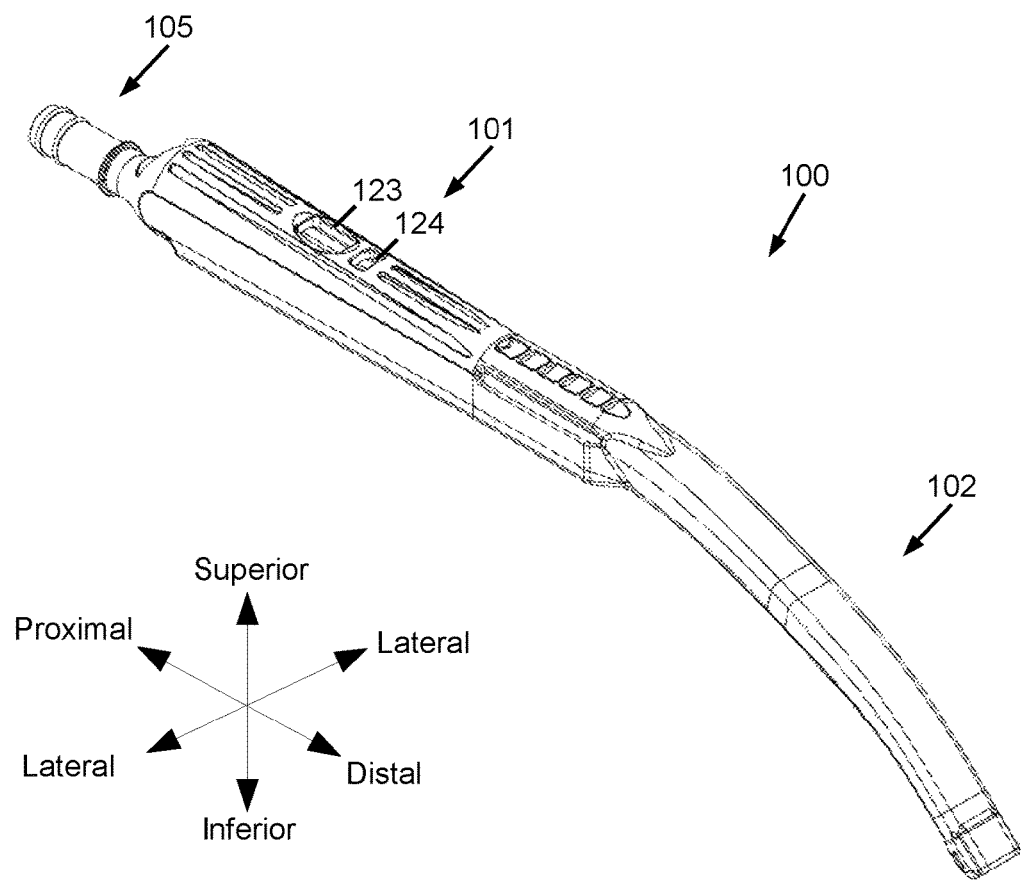
FIG. 1 shows a top perspective view of a tonsillectomy suction dissector apparatus in accordance with embodiments.

A tonsillectomy suction dissector apparatus 100 comprises a proximal handle 101 and a distal curved tip 102. The apparatus 100 comprises at least one suction channel 103 operably connecting at least one suction inlet port 104 located at an end of the tip 102 and a vacuum tube connection 105 located at the handle 101.

Reference will be made herein to the orientational axes provided in FIG. 1 wherein the apparatus 100 is elongate comprising a near/proximal and a far/distal end, side/lateral sides and top/superior and bottom/inferior sides.

Figure 7:
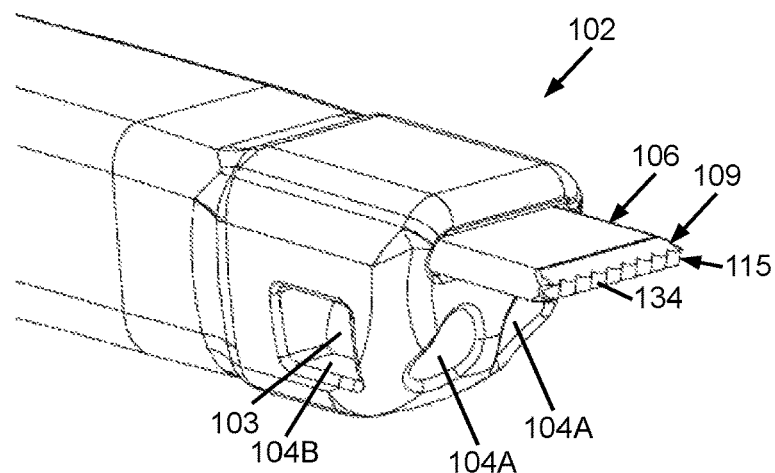
FIG. 7 shows a top perspective view of an end of the suction tip of the apparatus.
Figure 8:
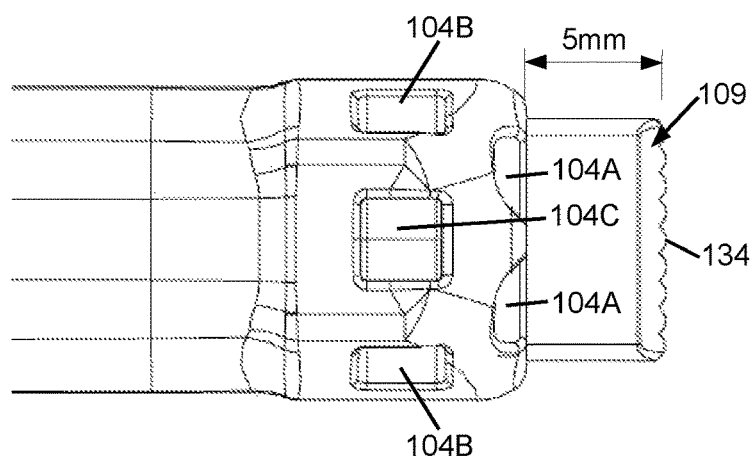
FIG. 8 illustrates a bottom plan view of the end of the suction tip.
Figure 9:
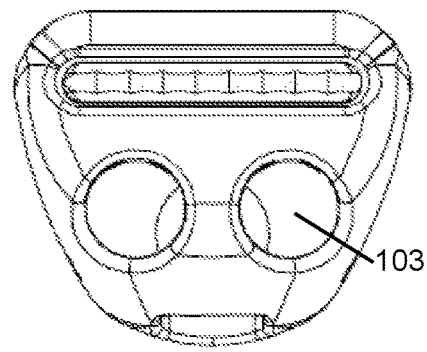
FIG. 9 illustrates a front elevation view of the end of the suction cup.
Figure 10:
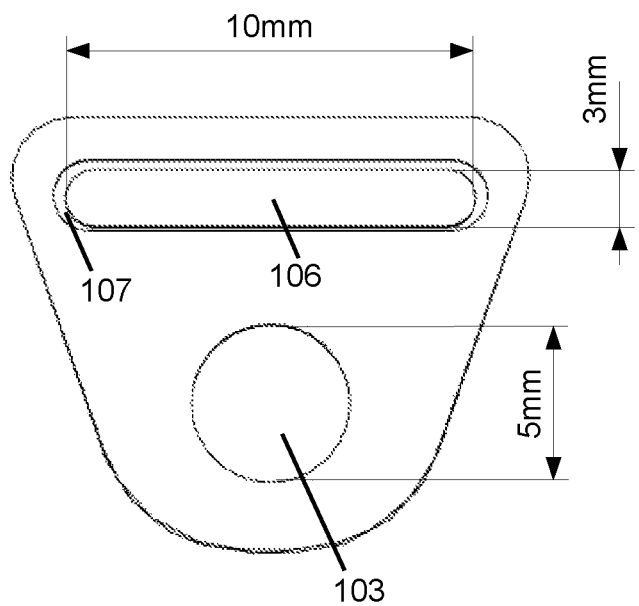
FIG. 10 illustrates a cross-sectional view of the tip of the apparatus.
Figure 11:
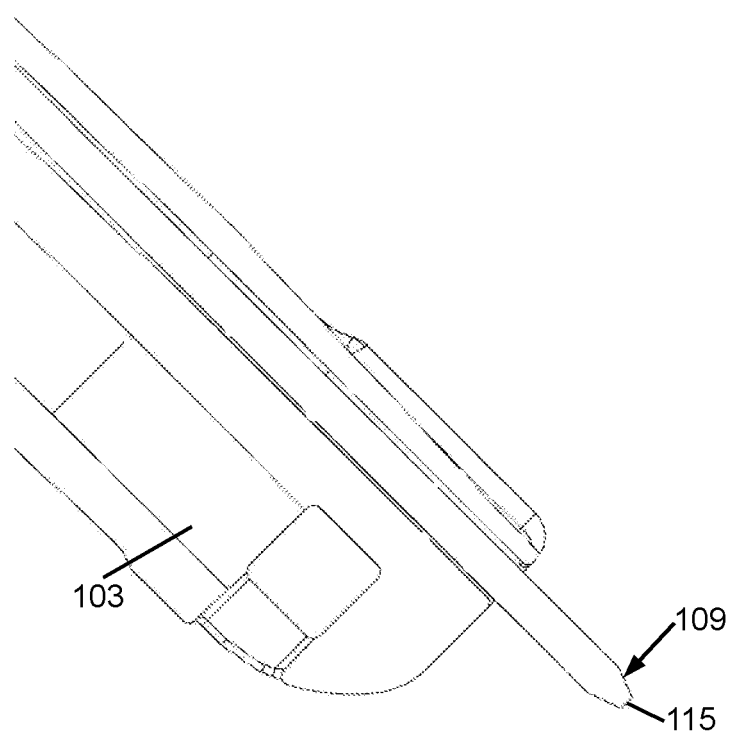
FIG. 11 illustrates a cross-sectional side view of the end of the tip of the apparatus.

The apparatus 100 further comprises a flexible cutting blade member 106 slidably retained within a slot 107 along the tip 102 and configurable by hand operable locking mechanism 108 at the handle 101 between an extended position wherein a distal cutting end 109 of the cutting blade member 106 protrudes from the end of the tip 102 as is substantially represented in FIGS. 7, 8 and 11, and a retracted position wherein the distal cutting end 109 is retracted within the end of the tip 102.

Utilisation of the apparatus 100 comprises the connection of suction apparatus to the vacuum tube connection 105. The curved tip 102 is then inserted from a left or right side into the mouth such that the end thereof locates at the back of the throat. The locking mechanism 108 may be configured to extend the distal cutting end 109 of the cutting blade member 106 from the end of the tip 102 such that the distal cutting end 109 is able to dissect the respective tonsil, typically whilst being pulled with a pair of forceps on the opposite hand. The distal cutting end 109 defines an orthogonal straight cutting edge 115 which may be pushed forwardly against the base of the tonsil while the tonsil is pulled in the opposite direction of the forceps, thereby dissecting the tonsil.

While dissecting, fluids may be drained through the suction inlet ports 104. At any time, the surgeon may employ the locking mechanism 108 to retract the distal cutting end 109 to employ the tip 102 for suction alone, extending the distal cutting end 109 when and as required.

The procedure may be repeated for the opposite tonsil by inserting the curved tip 102 from the opposite lateral side of the mouth.

In a preferred embodiment, the handle 101 and the tip 102 are integrally formed from plastic. Furthermore, so too in embodiments is the cutting blade member 106 made from plastic. However, in embodiments, the cutting blade member 106 may be flexibly formed from metal so as to be electrically conductive for electrocautery application. This will allow triple functionality as suction, dissection and electro cautery, and instantly sealing the bleeding points. Also, employing electric coagulation in the instrument will reduce the need of using force to dissect scarred tonsils as the electricity will dissolve scar tissue, coagulate while minimal dissection force is applied, leading to more precise dissection, less tissue trauma, thus quicker and less painful healing post operatively.

With reference to FIG. 4, the handle 102 may be generally elongate, thereby having an elongate axis and the tip 102 may curve from substantially in-line with the elongate axis of the handle 101 to deviate by approximately 40° therefrom at a distal end thereof. This 40° curvature, takes away the surgeons hands outside the operating field ensuring constant visibility, at the same time 40° smooth curvature maintained adequate suction power inside the suction port and prevent the blood clogging inside the suction port.

Figure 2:
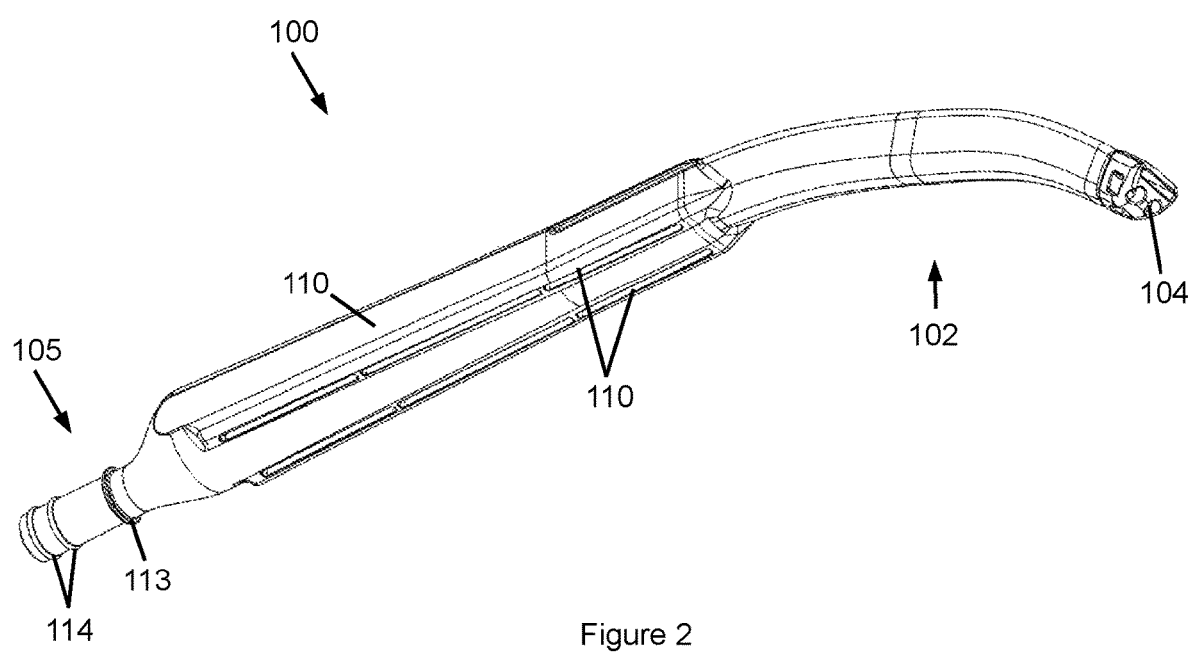
FIG. 2 illustrates a bottom perspective view of the apparatus.

With reference to FIGS. 1 and 2, the vacuum connection port 105 may extend from a proximal end of the handle 102. In the embodiment shown, the vacuum connection port 105 is generally cylindrical comprising an elongate axis substantially in line with an elongate axis of the handle 101. The vacuum connection port 105 may comprise connection interlock annuli 112 and O-ring seal 113.

FIG. 7 illustrates the end of the tip 102 in further detail showing the cutting blade member 106 in the extended position.

In a preferred embodiment shown, the cutting blade member 109 has a section which is flattened and orientated widthwise within the lengthwise slot 107 so as to be able to flex within the slot 107 when transitioning between the extended and retracted position. In one embodiment, the cutting blade member 109 may comprise a width of approximately 10 millimetres and a thickness of approximately 2 mm In a preferred embodiment, the cutting blade member 106 is manufactured from plastic.

As is illustrated in FIG. 7, the distal cutting end 109 may narrow to the orthogonal straight cutting edge 115.

Furthermore, the cutting edge 115 may comprise a plurality of serrations 134 running orthogonally across the cutting edge 115 from top to bottom which may engage the tonsil tissue to substantially prevent the cutting blade member 106 from slipping sideways during dissection and avoiding surrounding tissue damage.

As is best illustrated in FIG. 11, the cutting edge 115 is not sharpened to a point, thereby limiting the effectiveness of the cutting action thereof which may undesirably inadvertently damage surrounding tissue during manipulation, whilst yet comprising sufficient narrowness for being able to effectively cut the tonsils when required. For example, the width of the cutting edge 115 may be approximately 1 mm. Also, the blade dimensions are optimised to be big enough to dissect well, but small enough to maintain visibility, watching the surrounding tissues at all time to avoid collateral tissue damage.

With reference to FIG. 8, there is shown the distal cutting end 109 extending beyond the end of the tip 102 by approximately 5 mm in the extended position.

With reference to FIG. 7, there is illustrated the suction inlet ports 104 being located inferiorly with respect to the cutting blade member 106.

Furthermore, in a preferred embodiment, the suction inlet ports 104 may be located on multiple faces of the end of the tip 102 such as distally, laterally and inferiorly, thereby reducing likelihood of occlusion. Specifically, FIG. 7 shows the suction inlet ports comprising a pair of distal inlet ports 104A, a pair of opposite lateral suction inlet ports 104B and FIG. 8 shows an inferior inlet port 104C.

Figure 12:
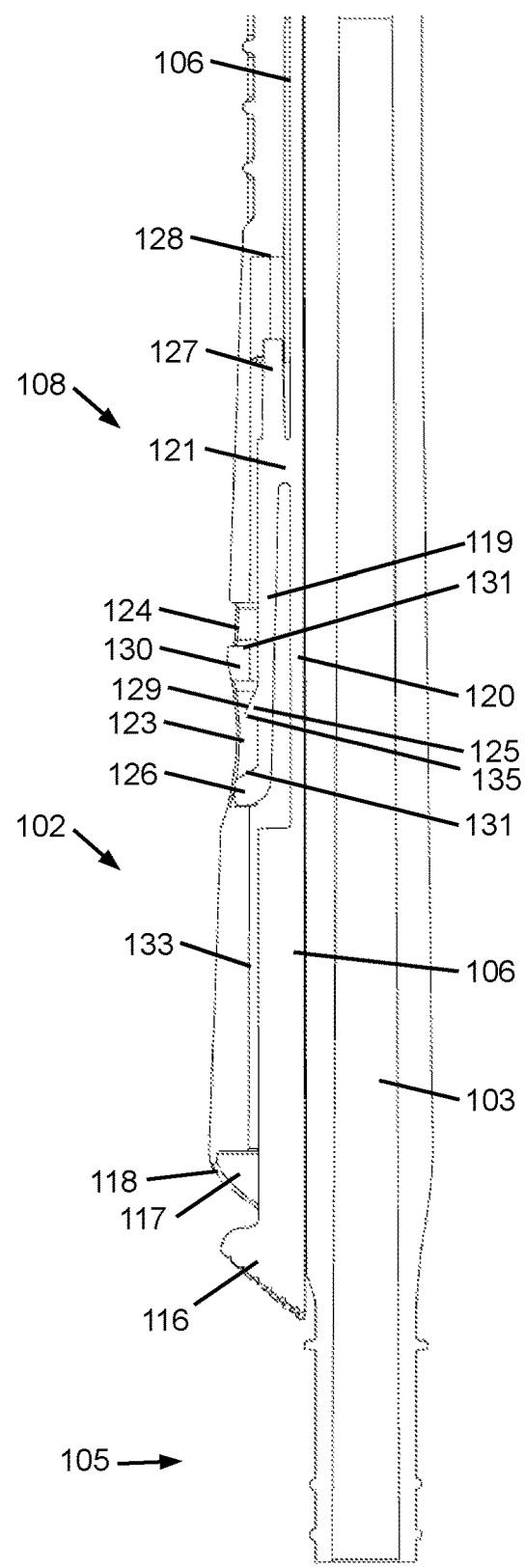
FIG. 12 illustrates a cross-sectional view of the handle of the apparatus.
Figure 13:
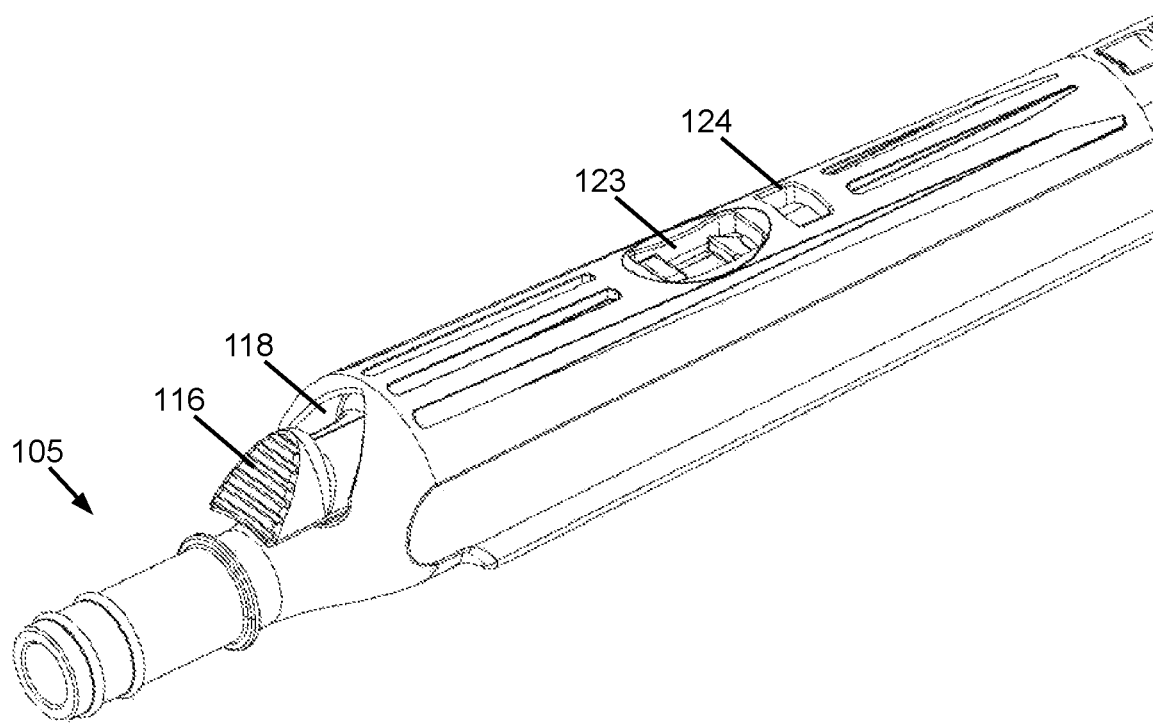
FIG. 13 illustrates the rearward position of the cutting blade member in the retracted position.
Figure 14:
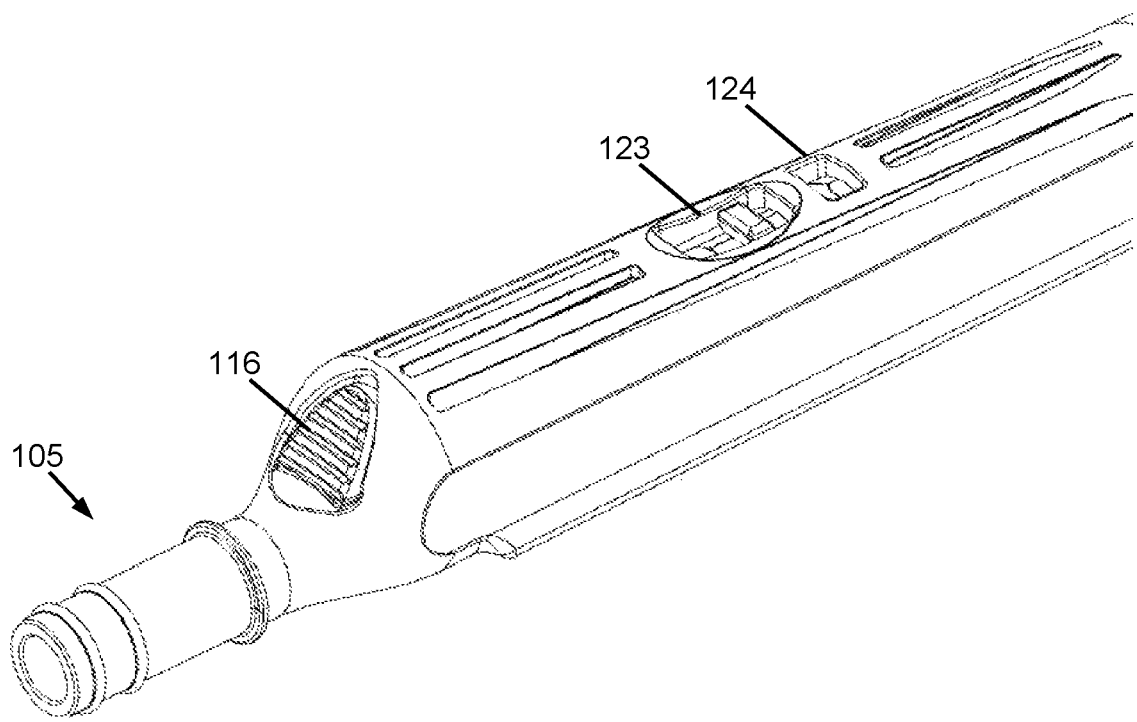
FIG. 14 illustrates the forward position of the cutting blade member in the extended position.

FIG. 12 illustrates a cross-sectional view of the apparatus 100 showing the locking mechanism 100 in further detail. As is shown, the cutting blade member 106 may comprise a proximal end 116 extending from a rearward aperture 117 of the handle 102. A proximal face of the proximal end 116 is angled so as to occupy and mate flush with the proximal surface 118 of the handle 102 when located forwardly.

The cutting blade member 106 further comprises a locking lever 119 pivotally coupled to an adjacent portion 120 by way of live hinge 121. Furthermore, a superior side 122 of the handle 102 comprises a major rearward aperture 123 and a minor forward aperture 124 between which an arrowhead boss 125 of the lever 119 is able to selectively transition. The lever 119 comprises a rearward knob 126 accessible via the major aperture 123 to depress the lever 119. Furthermore, the lever 119 terminates distally with buttress 127 which abuts against opposing wall 128 when the cutting blade member 106 is in the extended position.

FIG. 12 shows the cutting blade member 106 in the retracted configuration. As such, in order to extend the cutting blade member 109 for dissection, the rearward end 116 may be pushed forwardly along the elongate axis of the handle 102, typically with the thumb whilst grasping the underneath of the handle 102 with the forefingers. The forward ramp 129 of the arrowhead boss 125 depresses the lever 119 such that the arrowhead boss 125 is able to transition under the intermediate portion 130 between the major and minor apertures 123, 124 until such time that the arrowhead boss 125 locates within the forward minor aperture 124. Once in this location, the rearward orthogonal edge 135 of the arrowhead boss 125 jambs against a forward edge 131 of the intermediate portion 130, preventing the cutting blade member 106 from sliding rearwardly under pressure. At this extended position, the buttress 127 may abut against the opposing wall 128 thereby limiting the forward travel of the rearward end 116.

Subsequently, in order to retract the cutting blade member 106, the thumb may be inserted within the major aperture 123 to substantially depress the lever 119 and to simultaneously pull rearwardly against the forward edge 132 of the knob 126 which disengages the rearward face 130 of the arrowhead boss 125 from the forward edge 131 of the intermediate portion 130 and allowing the rearward sliding of the cutting blade member 106 under action of the thumb.

As can also be appreciated from FIG. 12, a rearward portion 133 of the slot 107 is sufficiently wide and so as to allow the entire rearward removal of the cutting blade member 106.

Whilst the locking mechanism 108 may be configured for thumb operation, the handle 102 may be shaped for enhancing the grip of the opposing forefingers. Specifically, with reference to FIG. 5, the panel 102 may comprise planar side walls and orthogonal inferior edges 111, conferring a non-circular cross-section to the handle 102, thereby preventing or reducing rotational slipping thereof within the surgeon's hand.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A tonsillectomy suction dissector apparatus comprising:
    a proximal handle and a distal curved tip;
    a suction channel within and along the tip operably connecting at least one suction inlet port located at the end of the tip to a vacuum port at the handle; and
    a flexible cutting blade member slidably retained within a slot within and along the tip and configurable by a hand operable locking mechanism between an extended position wherein:
    a distal cutting end of the flexible cutting blade member extends from the end of the tip and a retracted position;
    the distal cutting end of the flexible cutting blade member is retracted within the end of the tip; and
    the locking mechanism comprises:
        the cutting blade member comprising a locking lever able to be depressed via at least one superior aperture within the handle, the locking lever configured such that depressing the lever when the cutting blade member is in the extended position unlocks the cutting blade member to allow the cutting blade member to be retracted; and
        a proximal end of the cutting blade member extends via a rearward aperture of the handle, the rearward aperture facing rearwards, such that pushing the proximal end forwardly when the cutting blade member is in the retracted position slides the cutting blade member forwardly, wherein
    the at least one superior aperture comprises a rearward superior aperture and a forward superior aperture, distinct and separate from the rearward superior aperture, and wherein the lever comprises a rearward knob accessible via the rearward superior aperture and an arrowhead boss orientated to catch against a rear edge of the forward superior aperture when the cutting blade member is in the extended position and to slide under a front edge of the rearward superior aperture when the cutting blade member transitions from the retracted to the extended position.

2. Apparatus as claimed in claim 1, wherein the rearward superior aperture is sufficiently elongate such that the rearward knob locates between rearward and forward edges thereof between the retracted and extended positions.

3. Apparatus as claimed in claim 1, wherein the forward superior aperture is smaller than the rearward superior aperture.

4. Apparatus as claimed in claim 1, wherein the rearward knob comprises a forward edge accessible within the rearward superior aperture against which the cutting blade member can be pulled rearwardly to the retracted position.

5. Apparatus as claimed in claim 1, wherein the cutting blade member can be pulled entirely from the rearward aperture.

6. Apparatus as claimed in claim 1, wherein the lever is pivotally retained by a live hinge.

7. Apparatus as claimed in claim 1, wherein the lever comprises a forward buttress which abuts against an opposing wall when the cutting blade member is at the extended position.

8. Apparatus as claimed in claim 1, wherein the proximal end lies flush with the rearward aperture when the cutting blade member is at the extended position.

9. Apparatus as claimed in claim 1, wherein the flexible cutting blade member comprises a flattened portion flexibly orientated widthwise within the slot.

10. Apparatus as claimed in claim 1, wherein the flexible cutting blade member comprises plastic.

11. Apparatus as claimed in claim 1, wherein the flexible cutting blade member comprises a thickness of approximately 3 mm.

12. Apparatus as claimed in claim 1, wherein the flexible cutting blade member comprises a width of approximately 10 mm.

13. Apparatus as claimed in claim 1, wherein the apparatus comprises a two-piece construction comprising a first piece comprising the integrally formed handle and tip and a second piece comprising the cutting blade member.

14. Apparatus as claimed in claim 1, wherein the distal cutting end narrows towards an orthogonal straight cutting edge.

15. Apparatus as claimed in claim 14, wherein the cutting edge comprises a length of approximately 10 mm.

16. Apparatus as claimed in claim 14, wherein the cutting edge comprises serrations.

17. Apparatus as claimed in claim 16, wherein the serrations are arranged substantially along the width of the cutting edge and transition from top to bottom of the edge.

18. Apparatus as claimed in claim 1, wherein the at least one suction inlet port is located inferiorly with respect to the distal cutting end and wherein the at least one suction inlet port comprises a plurality of suction inlet ports comprising at least one of a distal inlet port, a lateral inlet port and an inferior inlet port.

19. A method of performing a tonsillectomy comprising:
    providing an apparatus as claimed in claim 1; and
    pushing, with one hand, the proximal end of the cutting blade member forwardly to perform simultaneous dissection and suction and retracting the cutting blade member by depressing the lever to perform suction only.

* * * * *